United States Patent
Eberly

(10) Patent No.: US 10,550,392 B2
(45) Date of Patent: Feb. 4, 2020

(54) DNA-BASED TESTING FOR ENVIRONMENTAL CONTAMINATION

(71) Applicant: Jed O. Eberly, Vicksburg, MS (US)

(72) Inventor: Jed O. Eberly, Vicksburg, MS (US)

(73) Assignee: UNITED STATES OF AMERICA AS REPRESENTED BY THE SECRETARY OF THE ARMY, Alexandria, VA (US)

(*) Notice: Subject to any disclaimer, the term of this patent is extended or adjusted under 35 U.S.C. 154(b) by 0 days.

(21) Appl. No.: 15/273,592

(22) Filed: Sep. 22, 2016

(65) Prior Publication Data

US 2018/0080025 A1 Mar. 22, 2018

(51) Int. Cl.
- *C12N 15/115* (2010.01)
- *C12Q 1/6825* (2018.01)
- *G01N 33/22* (2006.01)

(52) U.S. Cl.
CPC .......... *C12N 15/115* (2013.01); *C12Q 1/6825* (2013.01); *G01N 33/227* (2013.01); *C12N 2310/16* (2013.01)

(58) Field of Classification Search
CPC .................................................. C12N 15/115
See application file for complete search history.

(56) References Cited

U.S. PATENT DOCUMENTS

2007/0020641 A1* 1/2007 Heeger .................. B82Y 15/00
435/6.19
2008/0311677 A1* 12/2008 Chin ................ G01N 33/54326
436/526

OTHER PUBLICATIONS

Torshizi, et al. "Design of Aptamer-Based Detector for Trinitrotoluene (TNT) and Review of Its Performance." IJBR, v.7:2361-7. (Year: 2016).*

* cited by examiner

*Primary Examiner* — Jennifer Pitrak McDonald
(74) *Attorney, Agent, or Firm* — Brian C. Jones

(57) ABSTRACT

The present invention provides synthetic DNA aptamers that bind a target explosive to allow detection of that explosive. In various embodiments, the synthetic DNA aptamers may include one or more aptamers selected from the group consisting of SEQ ID 1-6. The various synthetic DNA aptamers are sensitive to different explosives. The synthetic DNA aptamers provide an inexpensive, in situ means for testing for explosive, which may be used for both soil and water samples. This testing may include an assay method using the synthetic DNA aptamers or a biosensor linked to the synthetic DNA aptamers.

4 Claims, 4 Drawing Sheets

Specification includes a Sequence Listing.

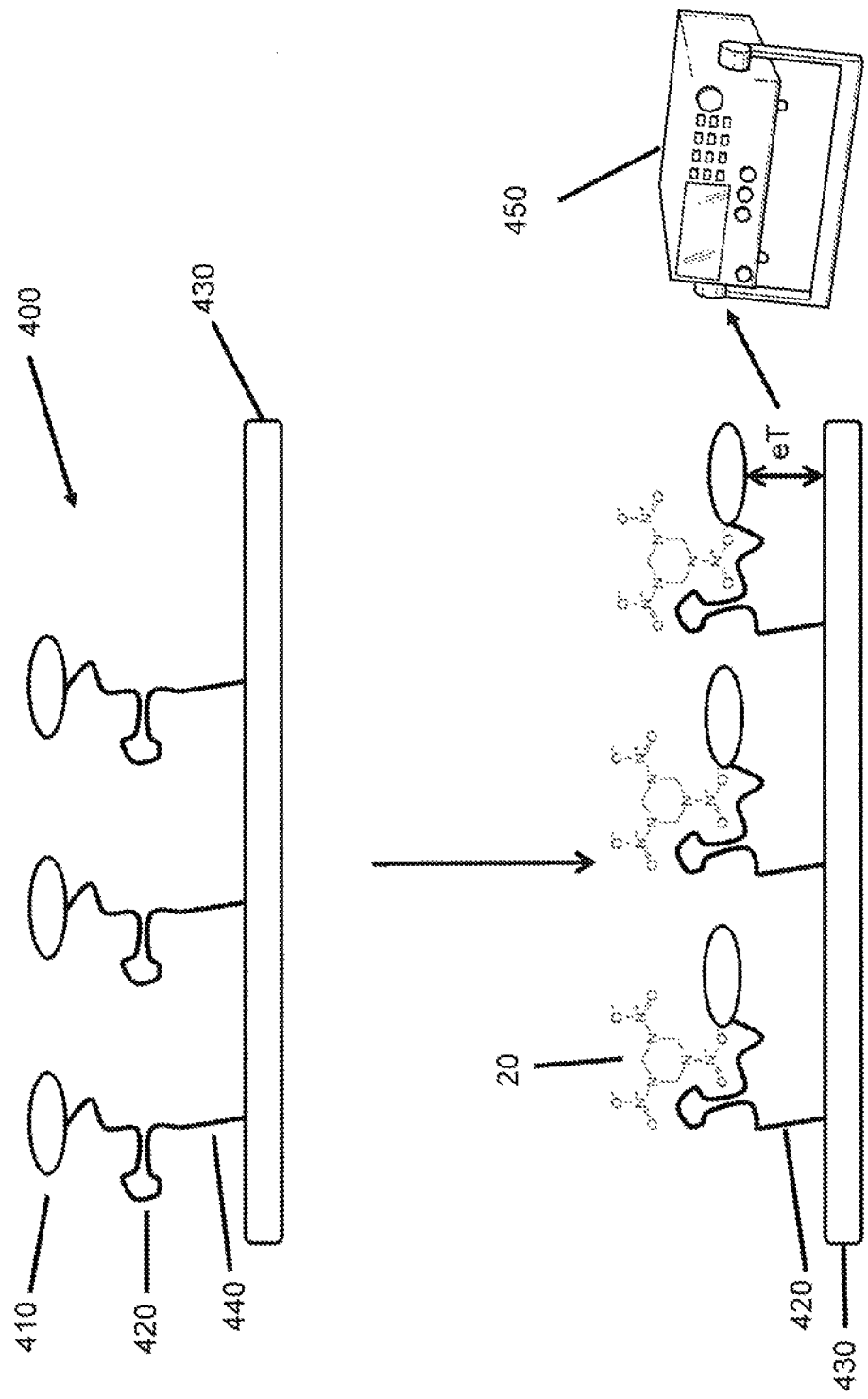

SEQUENCE LISTING

```
<160> NUMBER OF SEQ ID NOS: 6

<210> SEQ ID NO 1
<211> LENGTH: 76
<212> TYPE: DNA
<213> ORGANISM: Artificial sequence
<220> FEATURE:
<223> OTHER INFORMATION: Synthetic

<400> SEQUENCE: 1
tagggaagag aaggacatat gatacgaacg gtggcaactc ttgacgcaaa cccttgacta      60
gtacatgacc acttga                                                     76

<210> SEQ ID NO 2
<211> LENGTH: 76
<212> TYPE: DNA
<213> ORGANISM: Artificial sequence
<220> FEATURE:
<223> OTHER INFORMATION: Synthetic

<400> SEQUENCE: 2
tagggaagag aaggacatat gatacgaacg gtggcaactc ttgacgcaac ccttgactag      60
tacatgacca cttgaa                                                     76
```

```
<210> SEQ ID NO 3
<211> LENGTH: 75
<212> TYPE: DNA
<213> ORGANISM: Artificial sequence
<220> FEATURE:
<223> OTHER INFORMATION: Synthetic

<400> SEQUENCE: 3
tagggaagag aaggacatat gatacgaacg gtggaactct tgacgcaaac ccttgactag    60
tacatgacca cttga                                                    75

<210> SEQ ID NO 4
<211> LENGTH: 75
<212> TYPE: DNA
<213> ORGANISM: Artificial sequence
<220> FEATURE:
<223> OTHER INFORMATION: Synthetic

<400> SEQUENCE: 4
tagggaagag aaggacatat gatacgaacg gtggcaactc ttgacgccac ccttgactag    60
tacatgacca cttga                                                    75

<210> SEQ ID NO 5
<211> LENGTH: 76
<212> TYPE: DNA
<213> ORGANISM: Artificial sequence
<220> FEATURE:
<223> OTHER INFORMATION: Synthetic

<400> SEQUENCE: 5
taggggaaga gaaggacata tgatacgaac ggtggccctc ttgacgcaaa cccttgacta    60
gtacatgacc acttga                                                   76

<210> SEQ ID NO 6
<211> LENGTH: 76
<212> TYPE: DNA
<213> ORGANISM: Artificial sequence
<220> FEATURE:
<223> OTHER INFORMATION: Synthetic

<400> SEQUENCE: 6
tagggaagag aaggacatat gatacgaacg gtggcaattc ttgacgcaaa cccttgacta    60
gtacatgacc acttga                                                   76
```

US 10,550,392 B2

DNA-BASED TESTING FOR ENVIRONMENTAL CONTAMINATION

STATEMENT REGARDING FEDERALLY SPONSORED RESEARCH OR DEVELOPMENT

The invention described herein was made by an employee of the United States Government and may be manufactured and used by the Government of the United States of America for governmental purposes without the payment of any royalties thereon or therefore.

CROSS-REFERENCE TO RELATED APPLICATIONS

This application is a continuation-in-part and claims the benefit of U.S. patent application Ser. No. 14/729,732 filed Jun. 3, 2015. The above application is incorporated by reference herein.

INCORPORATION OF SEQUENCE LISTING

Incorporated by reference in its entirety herein is a computer-readable nucleotide/amino acid sequence listing submitted concurrently herewith and identified as follows: One 1,815 Byte ASCII (Text) file named "COE-714_DNA_SEQ.txt," created on Sep. 19, 2016.

FIELD OF INVENTION

This invention relates to the field of chemistry and more specifically to testing for explosives with a ligand-binding assay.

BACKGROUND OF THE INVENTION

Since World War II, an explosive known as C-4 has been widely used for military and civilian operations, such as excavation and demolition. C-4 contains an environmental contaminant known 1,3,5-Trinitroperhydro-1,3,5-triazine (RDX). RDX can migrate through soil and contaminate underlying groundwater aquifers and may be harmful to humans at relatively low levels. The US Environmental Protection Agency (EPA) has established a lifetime health advisory guidance level of 0.002 milligrams per liter (mg/L) for RDX in drinking water. The EPA has identified more than thirty RDX contaminated sites on its list of national clean-up priorities.

Manufacturers have begun to substitute a more stable chemical explosive, 3-Nitro-1,2,4-triazol-5-one (nitrotriazolone or NTO), for RDX. However, NTO faces similar problems with contamination. The US Center for Disease Control mandates reporting spills of any amount of NTO under the National Toxic Substance Incidents Program (NTSIP), requiring rapid testing of any areas where NTO may be present.

There are several problems known in the art for testing for the presence of RDX and NTO to make determinations relevant to a potential need for reporting and remediation. RDX and NTO concentrations are discrete particles that are irregularly dispersed throughout the soil. The concentration of samples from adjacent areas may vary considerably. Current RDX and NTO testing methods are intended to provide data about precise quantities of RDX and NTO using highly sensitive, off-site instrumentation to separately test each sample. This type of high-sensitivity off-site testing is not appropriate for wide scale EPA and private environmental remediation projects. The lack of rapid testing prevents immediate reporting under the NTSIP and often does not yield the necessary type of data for evaluating dispersal patterns over potentially contaminated site.

For purposes of reporting, planning, and remediation, it is important to be able to test many samples to determine the presence or absence of contaminants over a dispersed area and patterns of dispersal. Current high-sensitivity testing methods performed off-site are costly and prone to delay because they cannot be performed in situ.

There is an unmet need in the art for a rapid, in situ test for RDX and NTO contamination.

BRIEF SUMMARY OF THE INVENTION

This invention provides synthetic DNA aptamers that bind either of the explosives 1,3,5-Trinitroperhydro-1,3,5-triazine (RDX) or 3-Nitro-1,2,4-triazol-5-one (NTO). This enables inexpensive, in situ testing for these explosive chemicals. One such method for detecting the explosives involves admixing a buffered solution of one of the synthetic DNA aptamers with a sample in need of testing for explosives, and assaying the sample for explosives.

This invention also provides a biosensor apparatus which uses the synthetic DNA aptamers to test for explosives. The biosensor apparatus is made of multiple synthetic DNA aptamers. The synthetic DNA aptamers are modified to link to an electrode. The surface electrode is linked to the plurality of synthetic DNA aptamers.

BRIEF DESCRIPTION OF SEVERAL VIEWS OF THE DRAWING(S)

FIG. 4 is a schematic of an exemplary embodiment of a synthetic DNA aptamer electrical-chemical signal transducer.

TERMS OF ART

As used herein, the term "assay" is a test or testing for the quantity, presence, or absence of a substance.

As used herein, the term "synthetic DNA" refers to a DNA molecule that does not occur naturally.

As used herein, the term "synthetic DNA aptamer" refers to a DNA molecule that includes nucleotides having the chemical structure that binds a substance.

DETAILED DESCRIPTION OF THE INVENTION

Figure 1:
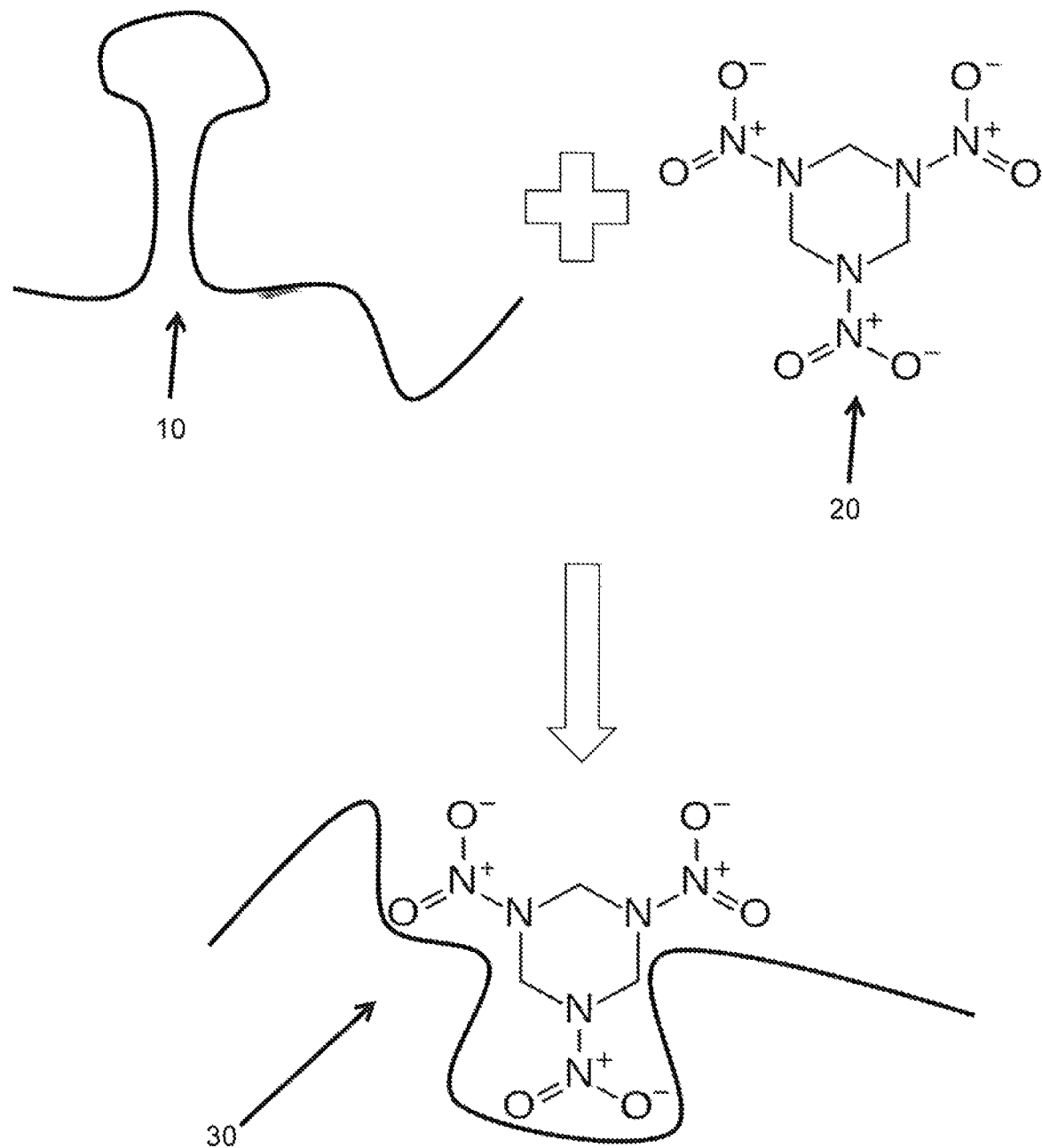
FIG. 1 is a schematic illustrating an exemplary embodiment of how a synthetic DNA aptamer binds to explosives.

FIG. 1 is a schematic illustrating how an exemplary embodiment of a synthetic DNA aptamer 10 binds to an explosive 20, such as RDX or NTO. In this exemplary embodiment, synthetic DNA aptamer 10 binds to explosive 20 by the formation of secondary structures. In this exemplary embodiment, explosive 20 is RDX. The combination of synthetic DNA aptamer 10 secondary structures and three-dimensional tertiary structures enables synthetic DNA aptamer 10 to bind target explosive 20. The combination of synthetic DNA aptamer 10 and explosive 20 forms a binding complex 30.

In the exemplary embodiment, synthetic DNA aptamer 10 is a 76 or 75 base-pair synthetic DNA aptamer including a thirty base pair binding region flanked by T7 promoter regions. In the exemplary embodiment shown, the use of T7 promoter regions simplifies the amplification steps during systematic evolution of ligands by exponential enrichment (SELEX) and sequencing. However, in alternate embodiments, other promoter region sequences may be used. The exemplary synthetic DNA aptamer 10 illustrated is developed by preparing a library of synthetic DNA sequences containing a thirty nucleotide variable region. This library was then subjected to multiple rounds of SELEX, to enrich for sequences that bind explosive 20.

Table 1 illustrates specific sequences of synthetic DNA aptamer 10 capable of binding explosive 20. The DNA sequence of the six synthetic aptamers form structures that have binding characteristics that allow them to bind to explosive 20. It should be noted that the sequences of synthetic DNA aptamers 10 can be modified by one skilled in the art to change, delete or add nucleotides to obtain synthetic DNA aptamers 10 that form structures that have binding characteristics that allow synthetic DNA aptamers 10 to bind to explosive 20. For example, the synthetic DNA aptamers 10 shown in Table 1 differ in sequence similarity by as much as 15 percent, but still have the desired binding characteristics that allow them to bind to explosive 20 and to form binding complex 30.

TABLE 1

Sequences of explosive binding synthetic DNA aptamers

| Clone | Sequence |
|---|---|
| 1 | TAGGGAAGAGAAGGACATATGATACGAACGGTGGCAACT CTTGACGCAAACCCTTGACTAGTACATGACCACTTGA SEQ ID NO. 1 |
| 2 | TAGGGAAGAGAAGGACATATGATACGAACGGTGGCAACT CTTGACGCAACCCTTGACTAGTACATGACCACTTGAA SEQ ID NO. 2 |
| 3 | TAGGGAAGAGAAGGACATATGATACGAACGGTGGAACTC TTGACGCAAACCCTTGACTAGTACATGACCACTTGA SEQ ID NO. 3 |
| 4 | TAGGGAAGAGAAGGACATATGATACGAACGGTGGCAACT CTTGACGCCACCCTTGACTAGTACATGACCACTTGA SEQ ID NO. 4 |
| 5 | TAGGGGAAGAGAAGGACATATGATACGAACGGTGGCCCT CTTGACGCAAACCCTTGACTAGTACATGACCACTTGA SEQ ID NO. 5 |
| 6 | TAGGGAAGAGAAGGACATATGATACGAACGGTGGCAATT CTTGACGCAAACCCTTGACTAGTACATGACCACTTGA SEQ ID NO. 6 |

One skilled in the art can prepare DNA oligonucleotides shown in Table 1 by enzymatic transcription or automated solid-phase synthesis. Enzymatic synthesis can produce relatively long transcripts in significant quantities, while commercial non-enzymatic DNA chemical synthesis can produce DNAs that are 40-80 nucleotides in length. Industrial scale production of DNA may be by chemical synthesis, by fermentation or by any other method known in the art for producing synthetic DNA.

Synthetic DNA aptamers 10 shown in Table 1 can be used to detect explosive 20 in soil and water samples. The sample tested for explosive 20 can include soil or water. Synthetic DNA aptamers 10 shown in Table 1 have binding characteristics that allow them to bind to explosive 20. These binding characteristics include high affinity and specificity for a specific explosive 20. Affinity refers to the tendency of a ligand molecule to bind to a biological molecule.

Figure 2:
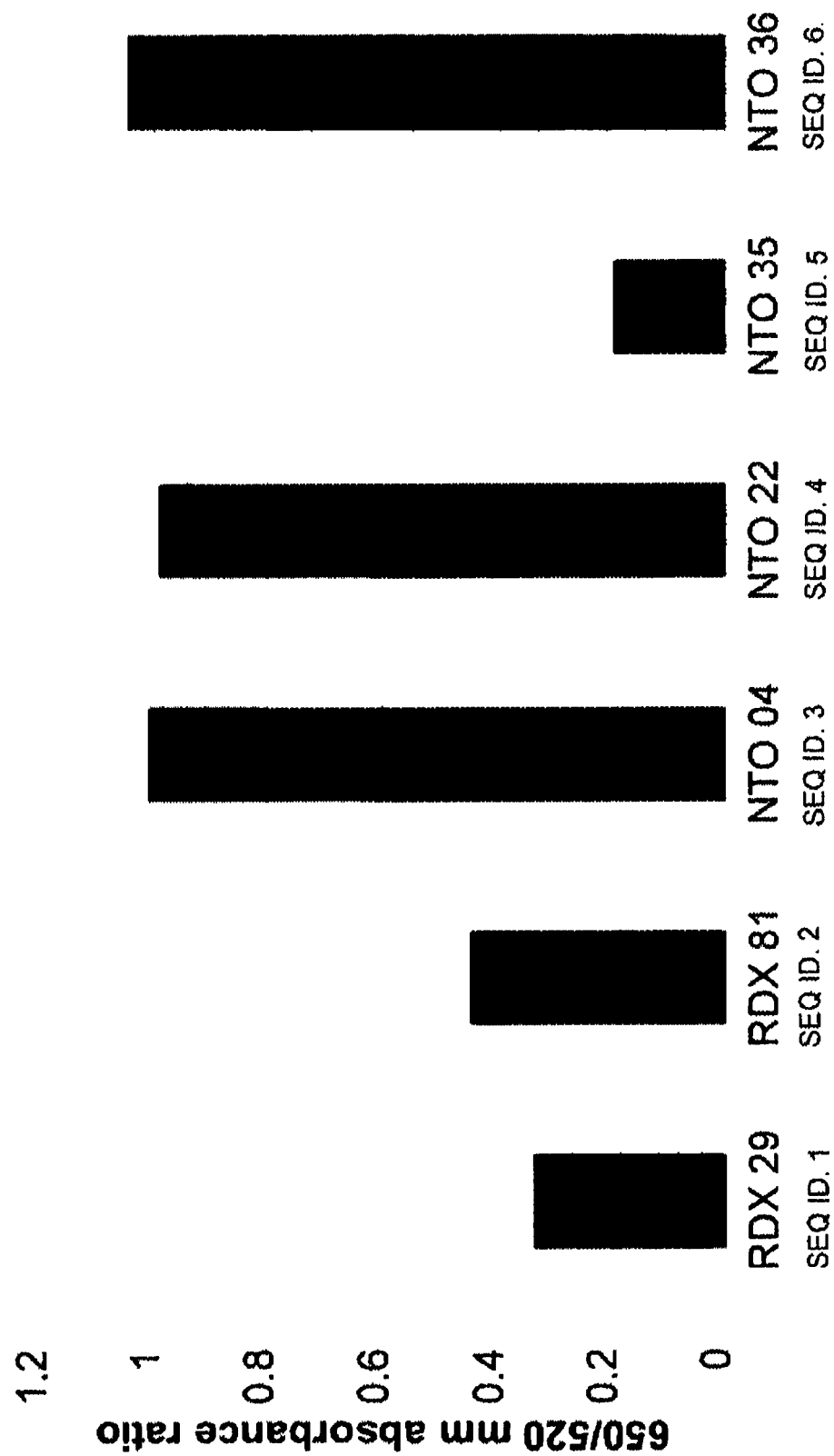
FIG. 2 is a graph illustrating the binding affinity of various embodiments of synthetic DNA aptamers for testing the presence of explosives.

FIG. 2 is a graph illustrating the binding affinity of various embodiments of synthetic DNA aptamers 10 for testing the presence of explosive 20 in a gold nanoparticle (AuNP) binding assay. This assay relies on a color change caused by the aggregation of AuNPs when the aptamer binds to the target. This color change can be measured by the ratio of light absorbance at 650 and 520 nm and is proportional to the amount of target explosive 20 present.

FIG. 2 shows the affinity of synthetic DNA aptamers 10 for target explosives 20 based on the absorbance ratio at 650/520 nm with 10 ppm of RDX or NTO. Synthetic DNA aptamers 10 display high affinity for explosive 20 with several clones capable of achieving almost an absorbance ratio of approximately 1:1. FIG. 2 assumes that there is a 1:1 molar ratio between the aptamer and target and that one synthetic DNA aptamer 10 will bind one molecule of explosive 20. In the exemplary embodiments shown, the AuNP absorbance ratio ranges from approximately 0.2 to approximately 1, with an absorbance ratio near 1 indicating nearly complete binding of the target by the aptamer.

Deriving the data in FIG. 2 required testing the binding affinity of synthetic DNA aptamers 10 using the following exemplary method.

5 microliters of 2 uM synthetic DNA aptamer 10 was combined with 5 microliters of phosphate buffer (pH 7) and denatured on a thermocycler for 15 minutes at 95° C. followed by cooling on ice for 5 minutes. The solution was transferred to a 1.5 mL microcentrifuge tube containing 90 microliters of gold nanoparticles and mixed for ten minutes at room temperature. In a separate 1.5 mL microcentrifuge tube, 10 microliters of 100 ppm (10 ppm final concentration) of the COI was dried under $N_2$, followed by the addition of the AuNP/aptamer mixture. The solution was mixed for twenty minutes at room temperature before the addition of 10 microliters of buffered salt solution (10 mM phosphate, 250 mM NaCl, pH 7.4). The solutions were mixed by vortexing the tube three to four times.

The absorbance measurements were taken at 520 and 650 nm before and after the addition of 10 microliters of 250 mM NaCl to calculate the 650/520 ratio which is an indication of the degree of aggregation of the AuNP. The absorbance was measured over time to determine the rate of reaction and to determine how long it took to achieve complete aggregation of the AuNP following addition of NaCl. Controls were NTO, DNAN, and TNT for RDX synthetic DNA aptamers 10 and RDX, DNAN, and TNT for NTO synthetic DNA aptamers 10. An additional control consisting of only AuNP and NaCl was run to determine the maximum 650/520 ratio based on complete aggregation of AuNP in the presence of NaCl.

Figure 3:
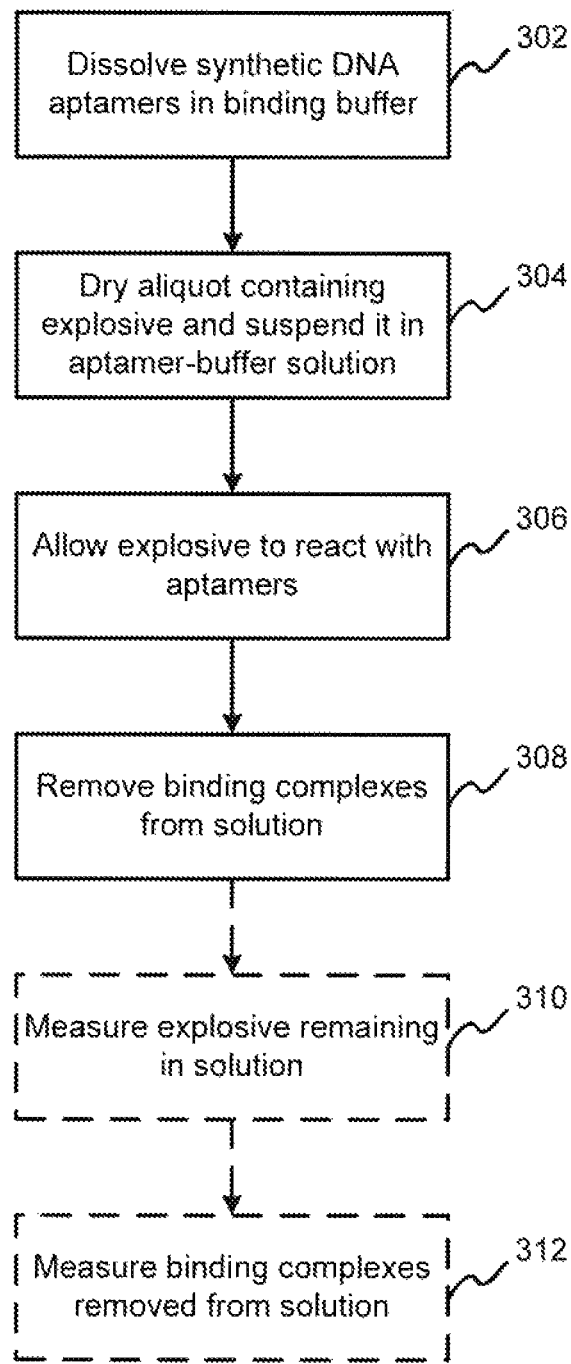
FIG. 3 is a flowchart of a method for measuring bound and/or unbound explosive.

FIG. 3 is a flowchart of method 300 for measuring bound and/or unbound explosive 20.

In step 302, method 300 dissolves synthetic DNA aptamers 10 in a binding buffer. In the exemplary embodiment, the binding buffer consists of sodium chloride (NaCl), magnesium chloride ($MgCl_2$), and Tris-HCl, and has a pH of 6.

In step 304, method 300 dries an aliquot containing explosive 20 and suspends it in the aptamer-buffer solution. Final concentrations of explosive 20 may range from 1-100 ppm.

In step 306, method 300 allows explosive 20 to react with synthetic DNA aptamers 10 to form binding complexes 30. In the exemplary embodiment, the reaction occurs for 1 hour at room temperature with constant stirring.

In step 308, method 300 removes binding complexes 30 from the solution. In the exemplary embodiment, this step is performed through centrifuging.

In optional step 310, method 300 measures explosive 20 remaining in solution. In the exemplary embodiment, such measurement utilizes high performance liquid chromatography (HPLC).

In optional step 312, method 300 measures binding complexes 30 removed from the solution.

One skilled in the art may use alternative methods to measure bound or unbound explosive 20. For example, in alternative embodiment, the assay can be an electrochemical assay platform. In another embodiment, synthetic DNA aptamer 10 is modified to covalently link to a detectable label and the detectable label is covalently linked to synthetic DNA aptamer 10.

FIG. 4 is a schematic of an exemplary embodiment of an electrical-chemical signal transducer 400 utilizing synthetic DNA aptamers 10. In this exemplary embodiment, explosive 20 is RDX. Transducer 400 includes a redox probe 410, a biosensor 420 and an electrode 430. In the exemplary embodiment shown, biosensor 420 is made of a bio-recognition layer including a plurality of synthetic DNA aptamers 10 that bind explosive 20. In this exemplary embodiment, synthetic DNA aptamers 10 are modified with a 5' C6 disulfide linker 440 for covalent attachment to the surface of electrode 430. In the exemplary embodiment shown, synthetic DNA aptamers 10 also have a 3'-amino modification to covalently attach redox probe 410, such as for example ferrocene (Fc).

In the exemplary embodiment shown, the addition of explosive 20 causes a conformational change in synthetic DNA aptamers 10, which changes the distance between redox probe 410 and a surface of electrode 430, which in turn changes the efficiency of electron transfer (eT). A potentiostat 450 measures the change in current over a voltage gradient. The amplitude of the current corresponds to the concentration of explosive 20. Potentiostat 450 is an electronic instrument that controls the voltage difference between a working electrode and a reference electrode.

A biological sensor can detect the existence of the target molecule within a relatively short time period. Biosensors are hybrid analytical devices that amplify signals generated from the specific interaction between a receptor, such as a binding region, and a ligand of interest, through a biophysical mechanism. Biosensors use nucleic acids as receptors, coupled to a physicochemical signal transducer.

In various embodiments, biological sensors can use chromatographic or enzymatic immunoassay detection techniques. A detectable label allows for the detection of a ligand. A label can be chemically linked or conjugated to the ligand or synthetic DNA aptamer 10. The detectable label can be a fluorescent label, a radioactive label, an enzyme label, or a redox label.

In one embodiment, the biosensor is an apparatus to detect explosive 20. The apparatus is made of a housing configured to receive a sample and to retain synthetic DNA aptamer 10. Synthetic DNA aptamer 10 with a 3'-amino modification binds to a detectable label such as ferrocene. In this way, the presence of the detectable label in the housing shows explosive 20 is present in the sample.

It will be understood that many additional changes in the details, materials, procedures and arrangement of parts, which have been herein described and illustrated to explain the nature of the invention, may be made by those skilled in the art within the principle and scope of the invention as expressed in the appended claims. It should be understood that the drawings are not necessarily to scale; instead, emphasis has been placed upon illustrating the principles of the invention.

What is claimed is:

1. A method for detecting an explosive comprising: admixing a buffered solution of a synthetic DNA aptamer that binds said explosive with a sample in need of testing for said explosive, and assaying said sample for said explosive wherein said synthetic DNA aptamer consists of one or more synthetic DNA aptamers selected from the group consisting of: SEQ ID 1-2 and wherein said explosive is RDX.

2. The method of claim 1 wherein said synthetic DNA aptamer is modified to covalently link to a detectable label and said detectable label is covalently linked to said synthetic DNA aptamer.

3. A method for detecting an explosive comprising: admixing a buffered solution of a synthetic DNA aptamer that binds said explosive with a sample in need of testing for said explosive, and assaying said sample for said explosive wherein said synthetic DNA aptamer consists of one or more synthetic DNA aptamers selected from the group consisting of: SEQ ID 3-6 and wherein said explosive is NTO.

4. The method of claim 3 wherein said synthetic DNA aptamer is modified to covalently link to a detectable label and said detectable label is covalently linked to said synthetic DNA aptamer.

* * * * *